United States Patent [19]

Robson

[11] Patent Number: 5,695,957
[45] Date of Patent: Dec. 9, 1997

[54] POLYPEPTIDES AND DNA ENCODING SAME, ASSOCIATED WITH HUMAN MALARIA PARASITES

[75] Inventor: Kathryn Jane Robson, Oxford, England

[73] Assignee: Imperial Exploitation Limited, London, England

[21] Appl. No.: 309,604

[22] Filed: Sep. 21, 1994

Related U.S. Application Data

[63] Continuation of Ser. No. 917,087, Aug. 4, 1992, abandoned.

[30] Foreign Application Priority Data

Feb. 5, 1990 [GB] United Kingdom .................. 9002512

[51] Int. Cl.$^6$ .................. C07K 14/435; C12N 1/21; C12N 15/12; C12N 15/63
[52] U.S. Cl. .............. 435/69.1; 435/252.3; 435/254.11; 435/320.1; 435/325; 435/348; 435/419; 514/12; 530/350; 530/395; 530/402; 536/23.5
[58] Field of Search .................. 435/69.1, 320.1, 435/240.2, 252.3, 254.11, 325, 348, 419; 530/350, 395, 402; 536/23.5

[56] References Cited

U.S. PATENT DOCUMENTS 4,707,357  11/1987  Dame et al. ................. 424/191.1
5,008,373  4/1991  Kingsman et al. ............ 530/350

OTHER PUBLICATIONS

Matsura et al., J. Gen. Virol. 68:1233–1250 (1987).

Robson et al., J. Cell. Biochem. Suppl. 13E:157 (1989).

Müller et al., EMBO J. 12(7):2881–2889 (93).

Robson, K.J.H. et al.; Nature 335:79–82 (1988).

*Primary Examiner*—Eric Grimes
*Attorney, Agent, or Firm*—Nixon & Vanderhye P.C.

[57] ABSTRACT

The invention provides proteins from the merozoite stage of the malaria parasite forming a conserved sequence in a broader sequence, fragments and derivatives thereof, DNA coding for the proteins and processes for the preparation of the proteins and plasmid and vital vectors useful in said processes. The invention also provides antibodies to the proteins and immunological compositions containing them.

32 Claims, No Drawings

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 342 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 1:

```
CAA GAT TCA TTA AAA GAA TCA AGA AAA TTA AGT GAT CGT GGT GTT AAA      48
Gln Asp Ser Leu Lys Glu Ser Arg Lys Leu Ser Asp Arg Gly Val Lys
 1               5                  10                  15

ATA GCT GTT TTT GGT ATT GGA CAA GGT ATT AAT GTA GCT TTC AAC AGA      96
Ile Ala Val Phe Gly Ile Gly Gln Gly Ile Asn Val Ala Phe Asn Arg
            20                  25                  30

TTT CTT GTA GGT TGT CAT CCA TCA GAT GGT AAA TGT AAC TTG TAT GCT     144
Phe Leu Val Gly Cys His Pro Ser Asp Gly Lys Cys Asn Leu Tyr Ala
        35                  40                  45

GAT TCT GCA TGG GAA AAT GTA AAA AAT GTT ATC GGA CCC TTT ATG AAG     192
Asp Ser Ala Trp Glu Asn Val Lys Asn Val Ile Gly Pro Phe Met Lys
    50                  55                  60

GCT GTT TGT GTT GAA GTA GAA AAA ACA GCA AGT TGT GGT GTT TGG GAC     240
Ala Val Cys Val Glu Val Glu Lys Thr Ala Ser Cys Gly Val Trp Asp
65                  70                  75                  80

GAA TGG TCT CCA TGT AGT GTA ACT TGT GGT AAA GGT ACC AGG TCA AGA     288
Glu Trp Ser Pro Cys Ser Val Thr Cys Gly Lys Gly Thr Arg Ser Arg
                85                  90                  95

AAA AGA GAA ATC TTA CAC GAA GGA TGT ACA AGT GAA ATA CAA GAA CAA     336
Lys Arg Glu Ile Leu His Glu Gly Cys Thr Ser Glu Ile Gln Glu Gln
                100                 105                 110

TGT GAA                                                              342
Cys Glu
```

( 2 ) INFORMATION FOR SEQ ID NO: 2:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Gln Asp Ser Leu Lys Glu Ser Arg Lys Leu Ser Asp Arg Gly Val Lys
 1               5                  10                 15
Ile Ala Val Phe Gly Ile Gly Gln Gly Ile Asn Val Ala Phe Asn Arg
             20                  25                 30
Phe Leu Val Gly Cys His Pro Ser Asp Gly Lys Cys Asn Leu Tyr Ala
         35                  40                 45
Asp Ser Ala Trp Glu Asn Val Lys Asn Val Ile Gly Pro Phe Met Lys
     50                  55                 60
Ala Val Cys Val Glu Val Glu Lys Thr Ala Ser Cys Gly Val Trp Asp
 65              70                  75                     80
Glu Trp Ser Pro Cys Ser Val Thr Cys Gly Lys Gly Thr Arg Ser Arg
                 85                  90                 95
Lys Arg Glu Ile Leu His Glu Gly Cys Thr Ser Glu Ile Gln Glu Gln
             100                 105                110
Cys Glu
```

( 2 ) INFORMATION FOR SEQ ID NO: 3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 3:

GGATCCAAAA TAATGAATCA TCTTGGG                                          27

( 2 ) INFORMATION FOR SEQ ID NO: 4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 4:

GGATCCGTAT TATATTTAAT TCCACTCG                                   28

( 2 ) INFORMATION FOR SEQ ID NO: 5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 5:

GGATCCATGG GTGTTAAAAT AGCTGTTTTT GGTATTGGAC                40

( 2 ) INFORMATION FOR SEQ ID NO: 6:

( i ) SEQUENCE CHARACTERISTICS:
        ( A ) LENGTH: 34 base pairs
        ( B ) TYPE: nucleic acid
        ( C ) STRANDEDNESS: single -continued ( D ) TOPOLOGY: linear ( i i ) MOLECULE TYPE: cDNA ( x i ) SEQUENCE DESCRIPTION: SEQ ID NO: 6:

GGATCCTTAT TCACTTGTAC ATCCTTCGTG TAAG    3 4

POLYPEPTIDES AND DNA ENCODING SAME, ASSOCIATED WITH HUMAN MALARIA PARASITES

This application is a continuation of application Ser. No. 07/917,087, filed Aug. 4, 1992, now abandoned, which was based on an International Application PCT/GB91/00162, filed Feb. 4, 1991, which claims priority from Application GB 9002512.3, filed Feb. 5, 1990.

This invention relates to polypeptides, and to DNA encoding same, associated with human malaria parasites. It also relates to methods of preparing the polypeptides, to antibodies thereto and compositions for use against malaria.

*Plasmodium falciparum* malaria is one of the most common infectious diseases in the world today, threatening up to 40% of the world's population. It is a disease of the Third World. There are between 150 and 300 million cases of this disease annually, over 1% of cases are fatal, babies and young children being the most vulnerable. With the advent of insecticides and new parasiticidal drugs developed after World War II it was felt that the disease could be eradicated. The early attempts proved very successful but with time the parasite has developed resistance to drugs such as chloroquine and the mosquito vector (*Anopheles*) has developed resistance to DDT. As a consequence of this it is necessary to develop new approaches to try to combat the disease. As immunity to the disease develops with increasing age, in endemic areas, a vaccine, together with new anti-malarials and insecticides need to be developed if the disease is to be eradicated.

Current research programmes, throughout the world, are involved in defining what antigens might form part of a useful vaccine. The complex life-cycle of the parasite means that a simple vaccine based on one antigen may not be adequate and that an effective vaccine will probably require antigens from different development stages.

The human malaria parasite, *Plasmodium falciparum*, has a complex life-cycle, during which different antigens are produced at particular developmental stages. The major antigen on the sporozoite surface is the circumsporozoite or CS protein, which probably determines the specificity of the interaction between the parasite and liver cells. CS protein contains two conserved amino acid sequences, known as regions I and II, which are separated by a repeating amino acid motif.

The cloning of the gene for this protein has permitted the development of various vaccines. To date vaccine trials using parts of the CS protein have proved disappointing. Immunity to sporozoites does not necessarily prevent the erythrocytic phase of the. life-cycle which is associated with clinical disease. Only one sporozoite needs to evade the immune system for clinical disease to occur. Currently CS protein is the only well-characterised protein known to be involved in host-cell recognition. The merozoite is the developmental stage capable of re-infecting fresh red cells. Antibodies which prevent gametocyte differentiation within the mosquito are useful in breaking the transmission cycle as well. Another complexity is the antigenic variation displayed by the parasite. A vaccine against the asexual erythrocytic parasite, need only be partially effective to reduce the severity of the disease. A vaccine against the asexual blood stages of *P. falciparum* has been developed by Patarroyo et al (Nature Vol.332, 1988, p158) based on the use of synthetic peptides, but this has not proved to be totally effective.

Robson et al (Nature. Vol 335 pp 79–82, 1988) have reported that polypeptides sharing certain sequence motifs with CS protein are produced during the erythrocytic stage of the parasite life-cycle. Such polypeptides and DNA encoding therefor also form the subject matter of co-pending published patent application PCT/GB 89/00895 (International Publication No. WO90/01496). One example is illustrated in formula I of the said patent application and in FIG. 2 on page 80 of the said Nature publication and is referred to therein and hereinafter by the abbreviation "TRAP" (thrombospondin-related anonymous. protein). The numbering system used herein for amino acid and nucleotide residues is the same as that of the said FIG. 2.

Comparisons of the nucleotide sequence in DNA's from several different isolates of *P. falciparum* have now been made. Considerable variation between isolates has been found, as would be expected for malaria, but one region of the DNA molecule has been found to be completely conserved in the isolates examined. It is likely, therefore, that the polypeptide sequence coded for by this region is significant for the biological properties of the polypeptide as a whole.

Accordingly, the present invention provides a polypeptide selected from the group comprising:

a) a polypeptide consisting essentially of or derived from the amino acid residue sequence 182–276 inclusive represented in Formula I (SEQ ID NO: 1 and SEQ ID NO: 2);

b) fragments of a) having essentially the same or related biological activity;

and derivatives of a) or b) having essentially the same or related biological activity.

Further the present invention provides a polypeptide selected from the group comprising:

a) a polypeptide consisting essentially of or derived from the amino acid residue sequence 221–276 inclusive represented in Formula I (SEQ ID NO: 1 and SEQ ID NO: 2);

b) fragments of a) having essentially the same or related biological activity; and derivatives of a) and b) having essentially the same or related biological activity.

Formula I (SEQ ID NO: 1 and SEQ ID NO: 2) represents a region of the "TRAP" protein which, for the purposes of the above definition, may be derived from any source (and is not confined to protein from isolate T9/96-Thailand) and which includes the polypeptide sequences 182–276 (overlined) and 221–276 of the invention. Sequence 182–276 is hereinafter referred to as the conserved sequence or region and sequence 221–276 as the inner conserved sequence or region respectively.

Although the present invention is based on the surprising discovery of the high degree of conservation within the above region of the "TRAP" molecule, it will be understood by those skilled in the art that the biological activity of this region may be tolerant of some changes in composition. Such changes, however, should be of a subtle or conservative character.

Biological activity of interest may include, for example, immunogenic activity, involvement in parasite recognition of red cells, red cell attachment or merozoite invasion. Activity may also include involvement in binding to sulphated glycoconjugates.

Fragments of the polypeptides of the invention which are likely to be of especial interest are those centred in or around the conserved region identified in the above referenced Nature paper, i.e. from residues 247 to 266 of Formula I (SEQ ID NO: 1 and SEQ ID NO: 2) herein.

The single letter symbols for amino acid residues (upper row) in Formula I (SEQ ID NO: 1 and SEQ ID NO: 2)

represent the following naturally occurring L-amino acids: (A) alanine, (C) cysteine, (D) aspartic acid, (E) glutamic acid, (F)phenylalanine, (G) glycine, (H) histidine, (I) isoleucine, (K) lysine, (L) leucine, (M) methionine, (N) asparagine, (P) proline, (Q) glutamine, (R) arginine, (S) serine, (T) threonine, (V) valine, (W) tryptophan, (Y) tyrosine.

Derivatives of the polypeptides of the invention are, for example, where functional groups, such as amino, hydroxyl, mercapto or carboxyl groups, are derivatised, e.g. glycosylated, acylated, amidated or esterified, respectively. In glycosylated derivatives an oligosaccharide is usually linked to asparagine, serine, threonine and/or lysine. Acylated derivatives are especially acylated by a naturally occurring organic or inorganic acid, e.g. acetic acid, phosphoric acid or sulphuric acid, which usually takes place at the N-terminal amino group, or at hydroxy groups, especially of tyrosine or serine, respectively. Esters are those of naturally occurring alcohols, e.g. methanol or ethanol.

Further derivatives are salts, especially pharmaceutically acceptable salts, for example metal salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine, and the like.

Further derivatives may include fusion derivatives having an additional amino acid residue sequence at either or each end or oligomeric forms of the polypeptide. Such derivatives may themselves be further derivatised as outlined above.

The present invention also provides DNA sequences coding for the polypeptides of the invention. One DNA sequence is displayed in Formula I (SEQ ID NO: 1 and SEQ ID NO: 2) but the scope of the present invention extends to variations not affecting the amino acids encoded.

DNA according to the present invention may be recovered from malaria parasite DNA and genomic libraries by methods known in the art and it will be understood that, since the sequence is known, direct amplification is possible, by the polymerase chain reaction, for example. (Saiki et al, Science 1985 Vol. 230 pp1350–1354 and PCR Technology. Ed. Erlich, Stockton Press, New York, USA, 1989.)

The polypeptides of the invention may be prepared by methods known in the art, for example, by chemical synthesis or by expression of the appropriate DNA sequences in a host/vector expression system.

Recombinant vectors comprising the appropriate DNA, together with other functional sequences, such as promoter and marker genes, may be made by methods known in the art.

Suitable vectors include recombinant plasmids comprising a DNA sequence of the present invention cloned, for example, into M13mp8 (Amersham), pUC13 (Pharmacia) or pAc YM1, (Inst. of Virology, Mansfield Road, Oxford, England).

Recombinant viral vectors may be obtained by incorporating the appropriate DNA sequence into viral DNA by methods known in the art. (See, for example, DNA Cloning, Volume II, D. M. Glover, published 1985, IRL Press, Oxford, England, and Molecular Cloning, A Laboratory Manual, 2nd Edition, Sambrook, Fritsch and Maniatis, Cold Spring Harbour, USA.) One suitable method, according to the present invention, involves the combination of a plasmid with a virus using a co-transfection process in a suitable host cell.

Using a suitable plasmid, for example, together with the *Autographa Californica* Nucleopolyhedrosis Virus (AcNPV) in *Spodoptera frugiperda* cells, recombinant virus containing DNA sequence of the present invention may be reproducibly isolated.

A plasmid pKKJ17 comprising the "TRAP" sequence has been deposited at the National Collections of Industrial and Marine Bacteria Limited (NCIMB), 23 St. Machar Drive, Aberdeen, AB2 1RY, United Kingdom, under Accession No. NCIMB 40164 and a virus vKKJ17 expressing the sequence has been deposited at the European Collection of Animal Cell Cultures (ECACC), Public Health Service Laboratory, Centre for Applied Microbiology and Research, Porton Down, Salisbury, Wiltshire, SP4 0JG, United Kingdom, under Accession No. 89071402. Both deposits were made on 14th Jul., 1989, in connection with Patent Application PCT/GB89/00895 (WO 90/01496).

According to a further aspect of the present invention we provide polyclonal or monoclonal antibodies to the polypeptides of the invention. The antibodies may be made by techniques known in the art (see for example: Antibodies, A Laboratory Manual, E. Harlow and D. Lane, Cold Spring Harbour 1988) and may be used, for example, to purify the polypeptides of the invention, as a passive vaccine for the treatment of patients with malaria and as diagnostic reagents.

The polypeptides of the invention are likely to be useful in the preparation of vaccines and the like against malaria. For this purpose they may be incorporated as active ingredients in suitable carriers, adjuvants, etc. possibly in combination with other immunologically active materials to provide protection against different stages of the malaria parasite.

They may also be useful as antagonists for inhibition of sequestration or of invasion of cells by the parasite.

The invention will now be described in more detail with reference to the accompanying formula and tables in which:

| | |
|---|---|
| Formula I | represents a region of the "TRAP" protein from malarial isolate T9/96 (Thailand) including a polypeptide sequence according to the invention (overlined) and DNA coding therefor; |
| Table I | lists the changes in deduced amino acid residues across a range of malarial parasite variants, relative to a consensus sequence, derived from isolate FCR3 (Rockerfeller); |
| Table II | sets out the origins of the parasite variants of Table I; |
| and Table III | lists changes in DNA corresponding to the changes in the amino acid residue listed in Table I. |

Reference should also be made to the numbering system for the amino acid and nucleotide residues for "TRAP" used in FIG. 2 of the Nature paper referred to above (Vol. 335, 1st September 1988, page 80).

Referring now to Formula I (SEQ ID NO: 1 and SEQ ID NO: 2), a short region of "TRAP" from T9/96 and associated DNA is represented, including the polypeptide sequence of the present invention with short additional sequences at each end. It has been found from DNA sequence analysis of ten laboratory isolates and three wild isolates that the deduced amino acid residue sequence from 182 to 276 inclusive is completely conserved, suggesting that it is significant for biological activity and may form the basis for approaches to the treatment or prevention of malaria. It is believed that the inner conserved sequence 221–276 in particular is conserved in malarial isolates.

Apart from this long conserved sequence it has been found that individual changes in nucleotide and amino acid residues occur with the relatively high frequency which is typical of other malarial genes. It will be noted, however, that there are further, shorter conserved sequences which may also be significant for biological activity, for example between acid residues 362 and 397, 422 and 451 and between 491 and 525.

Although Formula I relates mainly to the conserved sequence it also shows flanking sequences at each end and it will be understood by those skilled in the art that flanking sequences of limited extent may be present in both polypeptide and DNA whilst still retaining the benefits conferred by the invention.

Table I lists the amino acid residue changes using the "consensus" sequence of laboratory isolate, FCR3, as a reference sequence. It should be noted that the strain described in Formula I (SEQ ID NO: 1 and SEQ ID NO: 2) and FIG. 2 of the cited Nature paper is T9/96. Except where indicated in Table 1,FCR3 is the same as T9/96.

Table III lists changes in nucleotide residues of DNA, corresponding to the amino acid residue changes set out in Table 1. It is a summary of the amino acid substitutions in the form of nucleotide changes and where these occur within particular codons. There is only one silent nucleotide change; this is in K1 and is a T-C transition in the third position of the codon for $Cys^{273}$ and does not, as a consequence, alter the amino acid.

No alterations occur in the 95 amino acid residues in the conserved region, suggesting it is important for biological activity. It will be understood, however, by those skilled in the art that even so, there may be some toleration of minor variations of a subtle or conservative character. Such possibilities may include, for example, the substitution of T for S at position 251, of K for R at position 266 or of D for E at position 276.

EXPERIMENTAL DETAILS

1. Isolation and sequencing of DNA from different isolates

The polymerase chain reaction was used for the direct isolation of characterised genes from genomic DNA.

Two oligonucleotide primers were designed containing BamH 1 sites as well as the 5' and 3' ends of the "TRAP" genes. The sequences of these two primers were:

A (SEQ ID NO: 3) GGATCCAAAATA ATGAATCATCTTGGG

B (SEQ ID NO: 4) GGATCCGTATTATATTTA ATTCCACTCG the underlined sequences correspond to the end of the coding sequence. Primer A represents the coding strand and in primer B this is the complementary strand. The DNA amplified was a genomic malaria DNA. The reaction was set up as described by Saiki et al (Science 1985, 230, 1350–1354) utilising Tag 1 polymerase (1 mM oligonucleotide primers A and B, 10mM deoxynucleoside triphosphates and 100 ng of genomic malaria DNA). The cycle times and temperatures were 1' at 93° C., 1' at 37° C., 5' at 72° C., the numbers of cycles was 35. After amplification the complete reaction mix was extracted with phenol/$CHCl_3$, followed by gel filtration to remove the unused deoxynucleoside triphosphates. The ends of the DNA product were repaired using the Klenow fragment of deoxyribonuclease 1 and fresh deoxynucleoside triphosphates. The reaction was again terminated by phenol/$CHCl_3$ extraction and gel filtration using Sephadex G50/80. The 5' ends of the DNA were phosphorylated using T4 polynucleotide kinase and adenosine triphosphate. The reaction was terminated by phenol/$CHCl_3$ extraction and the DNA recovered by propan-2-ol precipitation. This material was used as the substrate of a ligation reaction using T4 DNA ligase and phosphatased Sma 1 cut M13mp8 (Amersham). Constructs containing the desired insert were obtained and their authenticity checked by DNA sequencing.

2. Isolation and amplification of DNA from Conserved fragment

The following exemplary scheme for the isolation and sequencing of DNA coding for polypeptides of the invention was carried out.

Two different primers for the polymerase chain reaction were constructed as follows:

GGATCCATGGGTGTTAAAATAGCT-GTTTTTGGTATTGGAC (SEQ ID NO: 5) (coding strand)

GGATCCTTATTCACTTGTACATCCTTCGTGTAAG (SEQ ID NO: 6) (complementary strand)

The polymerase chain reaction conditions were adjusted to give a 2' extension time at 72° C. as the amplified product is considerably shorter than 1.7 kb. The template for amplification is a subclone containing this sequence such as a RV9 (a subclone of "Trap" in M13).

The reaction was set up as described by Saiki et al (Science 1985, 230, 1350–1354) utilising Tag 1 polymerase [(1 mM) oligonucleotide primers A and B, 10 mM deoxynucleoside triphosphates and 1 ng of RV9. The cycle times and temperatures were 1' at 93° C., 1' at 37° C., 2' at 72° C., the number of cycles was 15–20. After amplification the complete reaction mix was extracted with phenol/$CHCl_3$, followed by gel filtration to remove the unused deoxynucleoside triphosphates. The ends of the DNA product were repaired using the Klenow fragment of deoxyribonuclease 1 and fresh deoxynucleoside triphosphates. The reaction was terminated by phenol/$CHCl_3$ extraction and gel filtration using Sephadex G50/80. The 5' ends of the DNA were phosphorylated using T4 polynucleotide kinase and adenosine triposphate. The reaction was terminated by phenol/$CHCl_3$ extraction and the DNA recovered by propan-2-ol precipitation. This material was used as the substrate of a ligation reaction using T4 DNA ligase and phosphatased Sma 1 cut $pUCl_3$ (Pharmacia) and phosphatased Sma 1 cut M13mp8 (Amersham). Constructs containing the desired insert were obtained and their authenticity was checked by DNA sequencing.

A minimum of two M13 clones containing the "TRAP" sequence were examined by dideoxy sequencing using a series of primers which enabled rapid analysis of the amplified and cloned DNA.

3. Expression of polypeptide

The constructs produced in 2 above can be used to produce polypeptides of the invention by the following proposed exemplary scheme.

The fragment generated by digestion of the construct described with the restriction enzyme BamH 1 can be cloned into the BamH 1 site of pAcYM1.

The fragment is suitably released from $pUCl_3$ by BamH 1 digestion demonstrating that the necessary restriction sites would permit transfer of the transplacement plasmid pAcYM1 (obtainable from the Institute of Virology, Oxford, England). A suitable construct could be digested with BamH 1 and Hae 111, the reaction terminated by phenol/$CHCl_3$ extraction, followed by ethanol precipitation. This digest can be carried out to prevent gel purification of the desired 300 bp BamH 1 fragment prior to religation with the Bam HI site of pAcYM1. A similar ligation and transformation can be carried out with the insert and the new vector pAcYM1. Again constructs containing the desired fragment can be obtained. The orientation of the insert containing the "TRAP" sequence relative to the polyhedrin promoter is suitably checked by restriction mapping and sequencing.

Using pAcYM1 containing the desired DNA sequence a transfection of

Spodoptera frugiperdacells may be performed as outlined below. 25ug of the appropriate plasmid together with 1 ug of caesium choloride purified *Autographa californica* Nucleopolyhedrosis virus (AcNPV) DNA are prepared in Hepes buffered saline pH 7.5 containing 10 mM glucose and 125 mMCaCl$_2$. A calcium/DNA complex is allowed to form over a 45 minute period prior to addition to freshly plated *Spodoptera frugiperda* cells ($1.5 \times 10^6$ cells) and incubation for 1 hr at room temperature. The DNA precipitate is removed, fresh medium (TC100) added and the cells incubated at 20° C. until a cytopathic effect is observed (3 days post transfection). The viruses produced by these cells should be both wild type AcNPV and recombinant AcNPV containing the "TRAP" gene. Plaque purification following titration permits the isolation of pure recombinant virus.

This is facilitated by the fact that wild type AcNPV has intact polyhedrin gene and so produces occluded plaques whereas recombinants do not. The differences between the two types of plaque can be visualised using light microscopy.

The new construct suitably produces a soluble protein which is releasable from infected cells by lysis with detergents or sonication. Further purification using monoclonal antibodies to this region should be possible. Alternatively, affinity chromatography on heparin agarose should permit purification of the conserved fragment.

4. Synthetic process for polypeptide

As an alternative to the processes proposed above, the polypeptides of the invention may be made by chemical synthetic methods from component amino acids.

Examples of such methods are described in "Peptide Synthesis" by Atherton, E., Clive, D. J. L., and Sheppard, R. C., J. C. S. Perkin 529–537 (1981).

A more specific example is described by Schneider, J. and Kent, S. B. H. (1988) Cell 54 363–8 who describe enzymatic activity of a synthetic 99 residue protein corresponding to the putative HIV-1 protease and by Wlodawer et al (1989) Science 245 616–621, who elucidate certain features of the crystal structure of the protease using X-ray crystallographic techniques.

FORMULA I

```
      171                                           181
  Q   D   S   L   K   E   S   R   K   L   S   D   R   G   V   K   I   A   V
 CAA GAT TCA TTA AAA GAA TCA AGA AAA TTA AGT GAT CGT GGT GTT AAA ATA GCT GTT
          191                                               201
  F   G   I   G   Q   G   I   N   V   A   F   N   R   F   L   V   G   C   H
 TTT GGT ATT GGA CAA GGT ATT AAT GTA GCT TTC AAC AGA TTT CTT GTA GGT TGT CAT
              211                                           221
  P   S   D   G   K   C   N   L   Y   A   D   S   A   W   E   N   V   K   N
 CCA TCA GAT GGT AAA TGT AAC TTG TAT GCT GAT TCT GCA TGG GAA AAT GTA AAA AAT
                  231                                           241
  V   I   G   P   F   M   K   A   V   C   V   E   V   E   K   T   A   S   C
 GTT ATC GGA CCC TTT ATG AAG GCT GTT TGT GTT GAA GTA GAA AAA ACA GCA AGT TGT
                          251                                       261
  G   V   W   D   E   W   S   P   C   S   V   T   C   G   K   G   T   R   S
 GGT GTT TGG GAC GAA TGG TCT CCA TGT AGT GTA ACT TGT GGT AAA GGT ACC AGG TCA
                              271                                   281
  R   K   R   E   I   L   H   E   G   C   T   S   E   I   Q   E   Q   C   E
 AGA AAA AGA GAA ATC TTA CAC GAA GGA TGT ACA AGT GAA ATA CAA GAA CAA TGT GAA
```

TABLE I

| | AMINO ACID RESIDUE NO. | | | | | | | | | | | | | | | | |
|---|---|---|---|---|---|---|---|---|---|---|---|---|---|---|---|---|---|
| | 39 | 46 | 49 | 66 | 83 | 90 | 91 | 92 | 98 | 116 | 119 | 128 | 130 | 134 | 139 | 177 | 179 | 181 |
| Lab Isolates | | | | | | | | | | | | | | | | | | |
| FCR3 | R | E | L | N | E | L | N | I | R | I | K | Y | R | S | Q | K | N | R |
| FCR3A2 | | | | | | | | | | | | | | | | | | |
| ITO | | | | | | | | | | | | | | | | | | |
| ITO4 | | | | | | | | | | | | | | | | | | |
| T9/96 | S | Q | | | D | V | | V | K | | R | | | T | | | S | |
| T9/94 | | | | | | A | S | V | | | | | | T | | | | |
| K1 | | | | | | | | | | | | | | | | | | |
| HB3A | | | | | K | | | A | | K | | | | T | | | | |
| 3D7A | | | | | | A | S | V | | | | | K | T | | | S | |
| 7901 | | | | | | A | S | V | | | | | | T | E | | | |
| Wild Isolates | | | | | | | | | | | | | | | | | | |
| GM14A/B | | | V | | D | V | | V | K | S | | F | | T | | N | | |
| GM2A/B | | | | | D | V | | V | K | | R | | | T | | | S | |
| GM49A | | | | | D | V | | V | K | | R | | | T | | | | L |
| | 277 | 287 | 290 | 297 | 311 | 312 | 314 | 317 | 318 | 319 | 337 | 340 | 341 | 359 | 360 |

TABLE I-continued

| | | | | | | AMINO ACID RESIDUE NO. | | | | | | | | | |
|---|---|---|---|---|---|---|---|---|---|---|---|---|---|---|---|
| Lab Isolates | | | | | | | | | | | | | | | |
| FCR3 | I | P | R | H | F | A | E | K | E | N | G | P | N | E | Q |
| FCR3A2 | | | | | | | | | | | | | | | |
| ITO | | | | | | | | | | | | | | | |
| ITO4 | | | | | | | | | | | | | | | |
| T9/96 | | | W | D | S | S | Q | E | | | D | | | | |
| T9/94 | L | | W | Q | | | | E | K | | D | | | | |
| K1 | L | | | | | | | E | | | | | K | Q | |
| HB3A | L | | W | | | | | | | | | | | | |
| 3D7A | L | L | | D | | | | | | | | | | | |
| 7901 | L | | W | Q | | | | E | K | | | | | | R |
| Wild Isolates | | | | | | | | | | | | | | | |
| GM14A/B | L | | | | | | | | N | | H | | | | |
| GM2A/B | L | L | | D | | | | | N | | | R | | | |
| GM49A | L | | | | | | | | N | | | R | | | |

| | 361 | 398 | 412 | 419 | 421 | 452 | 467 | 469 | 473 | 474 | 487 | 489 | 490 | 526 |
|---|---|---|---|---|---|---|---|---|---|---|---|---|---|---|
| Lab Isolates | | | | | | | | | | | | | | |
| FCR3 | E | H | S | P | K | R | Y | D | H | P | K | G | G | Y |
| FCR3A2 | | | | | | | | | | | | | | |
| ITO | | | | | | | | | | | | | | |
| ITO4 | | | | | | | | | | | | | | |
| T9/96 | K | | N | | | | | | | | | | E | |
| T9/94 | K | | | | | | | | | | | | | |
| K1 | | L | | | | | | | | | | | | |
| HB3A | | | Y | | | | | | Y | | | | | F |
| 3D7A | | | Y | A | | | | | | | | A | | |
| 7901 | K | | Y | | | | | | | | | | | |
| Wild Isolates | | | | | | | | | | | | | | |
| GM14A/B | | | Y | | | H | H | | Y | H | Q | | | |
| GM2A/B | | | Y | N | | H | H | N | | | | | E | |
| GM49A | | | Y | N | | H | H | N | | | | | E | |

TABLE II

| Parasite Isolates | Origin |
|---|---|
| T9/96 | Thailand |
| T9/94 | Thailand |
| K1 | Thailand |
| HB3A | Honduras |
| 3D7A | The Netherlands NF54 (Africa) |
| ITO | Brazil |
| ITO4 | Selected form of ITO |
| FCR3 | Gambia |
| FCR3A2 | clone FCR3 |
| 7901 | (Palo Alto) Uganda |

T9/96, T9/94, HB3A, 3D7A are all obtainable from David Walliker, WHO Registry of Standard Strains of Malaria Parasite, Dept. of Genetics, University of Edinburgh, United Kingdom.. The other isolates can be obtained from The Rockefeller University in New York. The DNA samples with GM designations were from children with malaria in the Gambia.

TABLE III

| Amino Acid residue number | Position of change of codon | Nucleotide change | Type of change |
|---|---|---|---|
| 39 | 1 | C -> A | Transversion |
| 46 | 1 | G -> C | Transversion |
| 49 | 1 | C -> G | Transversion |
| 66 | 3 | C -> A | Transversion |
| 83 | 3 | A -> T | Transversion |
| 90A (GCT) | 1 and 2 | C -> G, T -> C | Transition, Transversion |
| 90V (GTT) | 1 | C -> G | Transversion |
| 91 | 2 | A -> G | Transition |
| 92 | 1 | A -> G | Transition |
| 98 | 2 | G -> A | Transition |
| 116 | 2 | T -> G | Transversion |
| 119 | 2 | A -> G | Transition |
| 128 | 2 | A -> T | Transversion |
| 130 | 2 | G -> A | Transition |
| 134 | 2 | G -> C | Transversion |
| 139 | 1 | C -> G | Transversion |
| 177 | 3 | A -> T | Transversion |
| 179 | 2 | A -> G | Transition |
| 181 | 2 | G -> T | Transversion |
| 277 | 1 | A -> T | Transversion |
| 287 | 2 | C -> T | Transition |
| 290 | 1 | T -> C | Transition |
| 297D (GAT) | 1 | C -> G | Transversion |
| Q (CAA) | 3 | T -> A | Transversion |
| 311 | 2 | T -> C | Transition |
| 312 | 1 | G -> T | Transversion |
| 314 | 1 | G -> C | Transversion |
| 317E (GAA) | 1 | A -> G | Transition |
| N (AAC) | 3 | A -> C | Transversion |
| 318 | 1 | G -> A | Transition |
| 319 | 1 | A -> C | Transversion |
| 337 | 2 | G -> A | Transition |
| 340 | 2 | C -> G | Transversion |
| 341 | 3 | C -> A | Transversion |
| 359 | 1 | G -> C | Transversion |
| 360 | 2 | A -> G | Transition |

TABLE III-continued

| Amino Acid residue number | Position of change of codon | Nucleotide change | Type of change |
|---|---|---|---|
| 361 | 1 | G -> A | Transition |
| 398 | 2 | A -> T | Transversion |
| 412N (AAT) | 1 and 2 | T -> A, C -> A | Transversion, Transversion |
| Y (TAT) | 1 | C -> A | Transversion |
| 419 | 1 | C -> G | Transversion |
| 421 | 3 | A -> C | Transversion |

TABLE III-continued

| Amino Acid residue number | Position of change of codon | Nucleotide change | Type of change |
|---|---|---|---|
| 452 | 2 | G -> A | Transition |
| 467 | 1 | T -> C | Transition |
| 469 | 1 | G -> A | Transition |
| 473 | 1 | C -> T | Transition |
| 474 | 2 | C -> A | Transversion |
| 487 | 1 | A -> C | Transversion |
| 489 | 2 | G -> C | Transversion |
| 490 | 2 | G -> A | Transition |
| 526 | 2 | A -> T | Transversion |

I claim:

1. An isolated polypeptide consisting of amino acid residues 14 to 108 of SEQ ID NO: 2 or portion thereof that includes amino acid residues 34 to 108 of SEQ ID NO: 2 or glycosylated, acylated, amidated or esterified derivative thereof, or pharmaceutically acceptable salt thereof.

2. An isolated DNA sequence encoding the polypeptide of claim 1.

3. The isolated DNA sequence of claim 2 wherein said DNA sequence encodes amino acid residues 34 to 108 of SEQ ID NO: 2.

4. A fusion protein comprising the polypeptide of claim 1.

5. The isolated polypeptide as claimed in claim 1 wherein said polypeptide is glycosylated.

6. An oligomer of the polypeptide as claimed in claim 1.

7. The isolated polypeptide of claim 1 wherein said polypeptide consists of amino acid residues 34–108 of SEQ ID NO: 2 or derivative thereof wherein an amino, hydroxyl, mercapto or carbonyl group thereof is glycosylated, acylated, amidated, or esterified, respectively, or a pharmaceutically acceptable salt thereof.

8. An isolated DNA sequence consisting of bases 40 to 324 of SEQ ID NO: 1 or portion thereof that includes bases 100 to 324 of SEQ ID NO: 1.

9. A recombinant molecule comprising a vector inserted into which is a DNA sequence encoding a polypeptide consisting of amino acid residues 14 to 108 of SEQ ID NO: 2 or portion thereof that includes amino acid residues 34 to 108 of SEQ ID NO: 2.

10. The recombinant molecule as claimed in claim 9 wherein said vector is a plasmid.

11. The recombinant molecule as claimed in claim 10 wherein said plasmid is selected from the group consisting of M13mp8, pUC13 and pAcYM1.

12. The recombinant molecule as claimed in claim 9 wherein said vector is a virus.

13. The recombinant molecule as claimed in claim 12 wherein the virus is *Autographa californica* Nucleopolyhedrosis.

14. A host cell comprising the recombinant molecule of claim 9.

15. The host cell according to claim 14 wherein said cell is a *Spodoptera frugiperda* cell.

16. A process of producing a polypeptide consisting of amino acid residues 14 to 108 of SEQ ID NO: 2 or portion thereof that includes amino acid residues 34 to 108 of SEQ ID NO.: 2, comprising culturing the host cell according to claim 14 under conditions such that said DNA sequence is expressed and said polypeptide is thereby produced.

17. An isolated polypeptide consisting of amino acid residues 14 to 108 of SEQ ID NO: 2 or glycosylated, acylated, amidated or esterified derivative thereof, or pharmaceutically acceptable salt thereof.

18. An isolated DNA sequence encoding the polypeptide of claim 17.

19. A fusion protein comprising the polypeptide of claim 17.

20. The isolated polypeptide of claim 17 wherein said polypeptide is glycosylated.

21. An oligomer of the polypeptide as claimed in claim 17.

22. The isolated polypeptide of claim 17 wherein said polypeptide consists of amino acid residues 14–108 of SEQ ID NO: 2 or derivative thereof wherein an amino, hydroxyl, mercapto or carbonyl group thereof is glycosylated, acylated, amidated, or esterified, respectively, or a pharmaceutically acceptable salt thereof.

23. An isolated DNA sequence consisting of bases 40 to 324 of SEQ ID NO: 1.

24. A recombinant molecule comprising a vector inserted into which is a DNA sequence encoding a polypeptide consisting of residues 14 to 108 of SEQ ID NO: 2.

25. The recombinant molecule as claimed in claim 24 wherein said vector is a plasmid.

26. The recombinant molecule as claimed in claim 25 wherein said plasmid is selected from the group consisting of M13mp8, pUC13 and pAcYM1.

27. The recombinant molecule as claimed in claim 24 wherein said vector is a virus.

28. The recombinant molecule as claimed in claim 27 wherein said virus is *Autographa californica* Nucleopolyhedrosis.

29. A host cell comprising the recombinant molecule of claim 24.

30. The host cell according to claim 29 wherein the host cell is a *Spodoptera frugiperda* cell.

31. A process for producing a polypeptide consisting of residues 14 to 108 of SEQ ID NO: 2 comprising culturing the host cell according to claim 29 under conditions such that said DNA sequence is expressed and said polypeptide is thereby produced.

32. A composition comprising the isolated polypeptide of one of claims 17, 19, 1, 4, 21, 6, 22 and 7, and a pharmaceutically acceptable carrier.

* * * * *